(12) United States Patent
Knebel et al.

(10) Patent No.: US 6,329,543 B1
(45) Date of Patent: Dec. 11, 2001

(54) PROCESS FOR SYNTHESIS OF ISOBORNYL (METH) ACRYLATE

(75) Inventors: Joachim Knebel, Alsbach-Haehnlein; Doris Saal, Bensheim, both of (DE)

(73) Assignee: Roehm GmbH & Co KG, Darmstadt (DE)

( * ) Notice: Subject to any disclaimer, the term of this patent is extended or adjusted under 35 U.S.C. 154(b) by 0 days.

(21) Appl. No.: 09/564,452

(22) Filed: May 3, 2000

(30) Foreign Application Priority Data

May 6, 1999 (DE) .............................................. 199 20 796

(51) Int. Cl.$^7$ ..................................................... C07C 69/52
(52) U.S. Cl. ........................... 560/220; 560/217; 560/231
(58) Field of Search ................................... 560/220, 217, 560/231

(56) References Cited

U.S. PATENT DOCUMENTS 5,399,744    3/1995    Pfirmann et al. .

*Primary Examiner*—Gary Geist
*Assistant Examiner*—Hector M. Reyes
(74) *Attorney, Agent, or Firm*—Oblon, Spivak, McClelland, Maier & Neustadt, P.C.

(57) ABSTRACT

The present invention relates to processes for synthesis of isobornyl (meth)acrylate by reacting camphene with (meth) acrylic acid in the presence of sulfuric acid and at least one compound having inhibiting action. Aqueous sulfuric acid with an acid concentration in the range of 65 to 85 wt % is used. Isobornyl (meth)acrylate can advantageously be distilled from a mixture containing sulfuric acid in the presence of 2,6-di-tert-butyl-α-(dialkylamino)-p-cresol.

13 Claims, No Drawings

US 6,329,543 B1

PROCESS FOR SYNTHESIS OF ISOBORNYL (METH) ACRYLATE

BACKGROUND OF THE INVENTION

1. Field of the Invention

The present invention relates to processes for synthesis of isobornyl (meth)acrylate by reacting camphene with (meth) acrylic acid in the presence of sulfuric acid and at least one compound having an inhibiting action.

2. Discussion of the Background

Monomeric isobornyl (meth)acrylate is widely used in the manufacture of varnish binding agents. An example of how this compound is synthesized is the reaction of camphene with (meth)acrylic acid in the presence of an acidic cation-exchange resin. This type of synthesis is described, for example, in European Patent Application EP A 0718271 (Atochem) and in German Unexamined Application DE-OS 4419686 (Hoechst AG); both incorporated herein by reference. Although ion-exchange catalysis appears elegant at first sight, it has the disadvantage in industrial practice that the catalyst loses activity after repeated use. One possible explanation of this loss is that a polymer film is formed on the resin despite good process control. Even regenerative cleaning and activation, for example by washing with acid followed by drying with a suitable solvent such as acetone, does not restore the original activity level, and so the catalyst must be replaced after a few cycles of use.

It is also known that camphene can be reacted with (meth)acrylic acid in the presence of concentrated sulfuric acid to obtain isobornyl (meth)acrylate. The use of concentrated sulfuric acid as catalyst is described in, for example, Japanese Unexamined Application JP-OS-54/126293; incorporated herein by reference. It should be noted immediately, however, that the yield of about 80% described in the Japanese document was unattainable by far (see Comparison Example 2).

Moreover, a very large quantity of N,N'-diphenyl-p-phenylenediamine (about 8% relative to the acrylic acid) must be used in order to prevent undesired polymerization of the (meth)acrylate. The great majority of this inhibitor must be removed from the mixture, however, because the inhibitor prevents the desired polymerization of isobornyl (meth) acrylate.

Furthermore, the proposed inhibitor has a yellow color, and so for this reason already it must be separated as completely as possible. The required cleaning steps, such as multiple distillation, lower the yield to very small quantities of pure product. Attempts can be made to replace this inhibitor by other inhibitors or mixtures of compounds having inhibiting action, but a conversion of only about 10% is obtained.

OBJECTS OF THE INVENTION

In view of the prior art cited and discussed herein, one object of the present invention is to provide a process for synthesis of isobornyl (meth)acrylate by reacting camphene with (meth)acrylic acid in the presence of sulfuric acid, in which process high conversions are achieved without the need to use large quantities of N,N'-diphenyl-p-phenylenediamine, which is difficult to separate.

Another object of the invention is to provide an inhibitor combination that is effective in particularly small quantities.

Yet another object of the invention is to provide a process for distillation of isobornyl (meth)acrylate from a mixture containing sulfuric acid without causing polymerization of the isobornyl (meth)acrylate.

DESCRIPTION OF THE INVENTION

These objects are achieved by the herein described processes for synthesis of isobornyl (meth)acrylate.

In a first aspect of the present invention there is provided, by the fact that aqueous sulfuric acid with an acid concentration preferably in the range of 65 to 85 wt % is used, including all values and sub-ranges therebetween, a process for synthesis of isobornyl (meth)acrylate by reacting camphene with (meth)acrylic acid in the presence of sulfuric acid and at least one compound having inhibiting action, by means of which process the desired isobornyl (meth)acrylate is obtained particularly inexpensively in high yield and in pure form.

In a second aspect of the present invention there is provided, by the fact that distillation is performed in the presence of 2,6-di-tert-butyl-α-(dialkylamino)-p-cresol, a process for distillation of isobornyl (meth)acrylate from a mixture containing sulfuric acid, without causing polymerization of a large proportion of the isobornyl (meth)acrylate in the distillation flask.

The objects of the invention are achieved in excellent manner by each individual one of these two aspects.

In particular, the following advantages among others are achieved by the features according to the invention:

Processes according to the invention lead to very high conversions and high purity of the products.

Commercially available inhibitors can be used in the process according to the invention.

The process can be performed inexpensively, since high-priced ion-exchange resins do not have to be used.

Furthermore, in particularly preferred embodiments, such small quantities of compounds having inhibiting action are needed that they can be removed completely without relatively large yield losses.

As used herein the notation "(meth)acrylic acid" includes methacrylic acid, acrylic acid and mixtures of the two acids.

Isobornyl (meth)acrylate can be represented in general by formula (I)

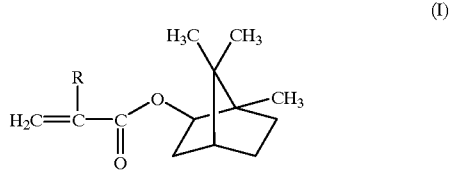

in which the group R denotes hydrogen or a methyl group.

Also covered by formula (I) are, in particular, isomeric forms of isobornyl (meth)acrylate that correspond, for example, to different positions of the acid group on the isobornyl ring.

The compounds camphene (2,2-dimethyl-3-methylenebicyclo[2.2.1]heptane), methacrylic acid and acrylic acid are widely known to those skilled in the art. These compounds can be obtained commercially from a large number of suppliers.

The same is true for aqueous sulfuric acid, which in the process according to the invention is used in an acid concentration in the range of 65 to 85 wt %, including 66, 67, 68, 69, 70, 72, 74, 75, 77, 79, 80, 81, 82, 83, and 84%, preferably 70 to 80 wt %, inclusive of all specific values between 70 and 80.

To prevent polymerization of the isobornyl (meth)acrylate or of the (meth)acrylic acid, it is preferred in the process according to the invention to use at least one compound having polymerization inhibiting action. Such compounds are widely known to those skilled in the art. Examples include hydroquinone alkyl ethers, sterically hindered phenols and/or sterically hindered piperidine N-oxyl derivatives.

Hydroquinone alkyl ethers can be represented by general formula (II)

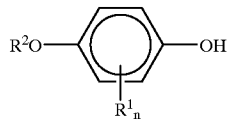

(II)

in which

R$^1$ denotes hydrogen, a straight-chain or branched alkyl group with one to eight carbon atoms, halogen or aryl, preferably an alkyl group with one to four carbon atoms, especially preferably methyl, ethyl, n-propyl, isopropyl, n-butyl, isobutyl, sec-butyl, tert-butyl;

n is an integer in the range of zero to four, preferably zero, one or two; and

R$^2$ denotes hydrogen, a straight-chain or branched alkyl group with one to eight carbon atoms or aryl, preferably an alkyl group with one to four carbon atoms, especially preferably methyl, ethyl, n-propyl, isopropyl, n-butyl, isobutyl, sec-butyl or tert-butyl.

Preferred sterically hindered phenols can be represented in general by the general structure (III)

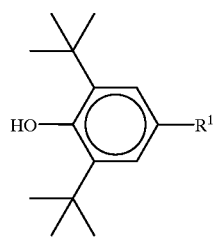

(III)

in which

R$^1$ denotes a straight-chain or branched alkyl group with 1 to 8 carbon atoms, aryl or aralkyl, propionic acid esters with monohydric to tetrahydric alcohols, which can also contain hetero atoms such as S, O and N, preferably a propionic acid ester with an octadecyl group.

A further advantageous substance class is represented by hindered phenols on the basis of triazine derivatives of formula (IV)

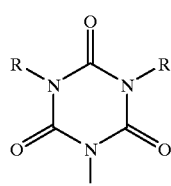

(IV)

with R=a compound of formula (V)

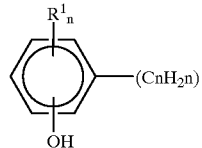

(V)

in which

R$^1$=C$_n$H$_{2n+1}$ with n=1 or 2.

Sterically hindered piperidine N-oxyl derivatives can be represented by, for example, formula (VI)

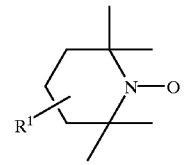

(VI)

in which R$^1$ denotes hydroxyl, an ether or an ester group, wherein the latter groups can have up to 20 carbon atoms. A plurality of sterically hindered piperidine N-oxyl groups can also be bonded via the group R$^1$.

Furthermore, compounds with 1,4-benzoquinone as the parent compound can also be used. These can be described with formula (VII)

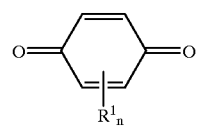

(VII)

in which

R$^1$ denotes a straight-chain or branched alkyl group with one to eight carbon atoms, halogen or aryl, preferably an alkyl group with one to four carbon atoms, especially preferably methyl, ethyl, n-propyl, isopropyl, n-butyl, isobutyl, sec-butyl, tert-butyl, Cl, F or Br; and n is an integer in the range of one to four, preferably one or two.

A further known inhibitor substance class is comprised by sterically hindered amines, such as N,N'-diphenyl-p-phenylenediamine.

Particular success is achieved by use of the compounds 1,4-dihydroxybenzene, 4-methoxyphenol, 2,5-dichloro-3,6-dihydroxy- 1,4-benzoquinone, 1,3,5-trimethyl-2,4,6-tris(3, 5-di-tert-butyl-4-hydroxybenzyl)benzene, 2,6-di-tert-butyl-4-methylphenol, 2,4-dimethyl-6-tert-butylphenol, 2,2-bis[3, 5-bis(1,1-dimethyl)-4-hydroxyphenyl-1-oxoperopoxymethyl)1,3-propandiyl ester, 2,2'-thiodiethylbis[3-(3,5-di-tert-butyl-4-hydroxyphenyl) propionate, octadecyl-3-(3,5-di-tert-butyl-4-hydroxyphenyl)propionate, 3,5-bis(1,1-dimethylethyl-2,2-methylenebis(4-methyl-6-tert-butyl)phenol, tris(4-tert-butyl- 3-hydroxy-2,6-dimethylbenzyl)-s-triazine-2,4,6-(1H, 3H,5H)trione, tris(3,5-di-tert-butyl-4-hydroxy)-s-triazine-2, 4,6-(1H,3H,5H)trione, tert-butyl-3,5-dihydroxybenzene, 2,6-di-tert-butyl-α-(dimethylamino)-p-cresol, 4-hydroxy-2, 2,6,6-tetramethylpiperidine N-oxyl and N,N'-diphenyl-p-phenylenediamine. It is also possible to use mixtures of these substances with great success.

It is particularly preferable to use inhibitors with high boiling points, since they can be separated particularly easily by distillation. In order to achieve the most desirable results it is very important that the compounds having inhibiting action that are present during the reaction be separated from the end product, since otherwise the quantity of initiator for polymerization of the isobornyl (meth)acrylate could vary. If the quantity of inhibitor is too large, polymerization no longer takes place even in the presence of very high initiator concentrations. Aside from economic considerations, this is an important reason to use the smallest possible quantity of compounds having inhibiting action. The minimum quantity of substances having inhibiting action is determined by their ability to act as radical traps. Guidelines in this regard can be obtained from, for example, the manufacturers, and the person of ordinary skill in the art can determine suitable quantities, for example without undue effort and by a very limited number of routine experiments.

In particularly surprising manner, it was found by the inventors through extensive experiments that, in the combined use of at least one hydroquinone alkyl ether, one sterically hindered phenol and one sterically hindered piperidine N-oxyl derivative, the quantities of the individual compounds can be kept particularly low.

For example, 100 to 500 ppm of hydroquinone monomethyl ether, 500 to 2000 ppm of octadecyl-3-(3,5-di-tert-butyl-4-hydroxyphenyl)propionate and 5 to 30 ppm of 4-hydroxy-2,2,6,6-tetramethylpiperidine N-oxyl, each relative to the total quantity of reaction mixture, are sufficient to prevent undesired polymerization during the reaction.

Iron ions can have a detrimental effect on the reaction according to the invention. To ensure that the iron ion concentration is as low as possible, a chelating agent can be used. This is advantageous in particular when technical sulfuric acid or a stainless-steel reactor is used. Chelating agents are widely known to those skilled in the art. It has proved particularly preferable to use nitrilotriacetic acid, ethylenediaminetetraacetic acid, N-(2-hydroxyethyl) ethylenediaminetriacetic acid, 1,2-cyclohexylenedinitrilotetraacetic acid, diethylenetriaminepentaacetic acid, 3,6-dioxaoctamethylenedinitrilotetraacetic acid and/or an alkali metal salt, such as a lithium, sodium, potassium and/or rubidium salt of these acids. These substances can be obtained relatively inexpensively.

The quantity of chelating agent used depends on the possible iron ion concentration. In general, however, a quantity larger than 500 ppm, preferably not larger than 2000 ppm relative to the total quantity of reaction mixture is sufficient. The reaction according to the invention can take place under normal, reduced or elevated pressure. Accordingly, the reaction temperatures can be selected in a wide range, generally as a function of the pressure used. Advantageous temperatures lie, for example, in the range of 50 to 90° C., inclusive of all values and sub-ranges therebetween, especially 60 to 80° C.

The reaction can be performed either continuously or in batches. The process according to the invention can be performed in the bulk substance, or in other words without using a further solvent. If desired, there can also be used an inert solvent such as benzene, toluene, n-hexane, cyclohexane, methyl isobutyl ketone and methyl ethyl ketone, among others.

The reaction times depend, for example, on the selected parameters such as pressure and temperature. In many cases, however, they lie in the range from one to 12 hours, preferably from three to eight hours.

The reaction mixture can be purified in any way familiar to the person skilled in the art. Especially preferred, however, is distillation according to the second aspect of the present invention. In this connection the distillation is performed in the presence of 2,6-di-tert-butyl-$\alpha$-(dialkylamino)-p-cresol. The preferred derivative is 2,6-di-tert-butyl-$\alpha$-(dimethylamino)-p-cresol. This substance having inhibiting action is used preferably in a quantity ranging from 250 to 1000 ppm relative to the total quantity of reaction mixture. Certainly it is entirely possible to use larger quantities, provided care is taken that such quantity does not pass over into the distillation receiver. Such a quantity, however, is not economically practical.

Apart from p-cresol, other compounds having inhibiting action can also be added. These include in particular the inhibitors mentioned hereinabove. The distillation is preferably performed at reduced pressure, or in other words a pressure below 200 mbar, preferably below 150 mbar and especially preferably below 130 mbar, in order to minimize the thermal stress on the end product. The distillation temperature depends on the pressure used, in that the required temperature becomes lower as the pressure is reduced. Preferably the distillation temperature is below 150° C.

The following example and the comparison example are provided in order to further describe the present invention, but are not intended to have limitative effect. The values in % are relative to the total weight unless otherwise indicated.

EXAMPLE 1

In a 500 ml four-necked flask with mechanical stirrer, internal thermometer, top-mounted reflux condenser and gas-inlet tube for introduction of air there was placed 238 g (1.75 mol) of camphene. There were then added 166 g (1.925 mol) of (meth)acrylic acid and, as compound having inhibiting action, 0.08 g (200 ppm) of hydroquinone monomethyl ether, 0.4 g (1000 ppm) of octadecyl-3-(3,5-di-tert-butyl-4-hydroxyphenyl)propionate, 0.008 g (20 ppm) of 4-hydroxy-2,2,6,6-tetramethylpiperidine N-oxyl and 0.4 g (1000 ppm) of Titriplex III (ethylenedinitrilotetraacetic acid disodium salt, Merck). Under stirring and introduction of air, there was mixed in 10.7 g (0.082 mol) of 75% sulfuric acid, during which the mixture turned brown. It was then heated to 70° C. and stirred for 4.5 hours, resulting in a final conversion of 70% (determined by titration with ethanolic KOH against phenolphthalein).

The mixture was cooled to room temperature and neutralized with 5 g (0.09 mol) of calcium oxide under stirring for 30 minutes. Then there were added a further 8 mg (20 ppm) of 4-hydroxy-2,2,6,6-tetramethylpiperidine N-oxyl, 0.2 g (500 ppm) of N,N'-diphenyl-p-phenylenediamine and 0.2 g (500 ppm) of 2,6-di-tert-butyl-$\alpha$-(dimethylamino)-p-cresol, and the unfiltered raw ester was purified by distillation over a 20 cm Vigreux column at a temperature in the distillation flask of 100 to 140° C. and a pressure of 130 to 5 mbar, the pressure being adjusted downward to compensate for the distillation rate, in order to achieve a constant distillation rate. There was now obtained 35 g of first runnings, which according to GC contained 62.8% camphene, 26.9% (meth)acrylic acid and 7.6% isobornyl (meth)acrylate, as well as 234 g (conversion yield 93.6%) isobornyl methacrylate with a gas chromatographically determined purity of 97.6%.

Comparison Example 1

Comparison Example 1 was performed in the same way as Example 1, except that 8.08 g (0.083 mol) of concentrated sulfuric acid was added instead of 75% sulfuric acid. During distillative purification of the raw ester there was obtained 51 g of first runnings, which according to GC consists of 71.4% camphene, 13.7% (meth)acrylic acid and further unknown products, and 24 g of main fraction, which according to GC contains 14.6% camphene, 67% (meth)acrylic acid and 13.3% isobornyl (meth)acrylate, at which point distillation ceased. The mixture in the distillation flask was highly viscous in this case, indicating polymerization.

Comparison Example 2

This comparison example was performed using the procedure of Synthesis Example 1 of Japanese Application Disclosure JP-OS-54/1266293. To 272 g of camphene there were added 176 g (2.08 mol) of methacrylic acid and 12 g (27000 ppm) of N,N'-diphenyl-p-phenylenediamine. Then a total of 6.5 g (0.065 mol) of concentrated sulfuric acid (98%) was slowly added dropwise thereto and the mixture was stirred for a further 2 hours at room temperature. Thereafter the reaction mixture was neutralized with 6.9 g (0.065 mol) of sodium carbonate.

Analysis of the mixture with gas chromatography indicated 69.37% camphene, 22.29% methacrylic acid, 1.49% isoborneol and 6.39% isobornyl methacrylate. Since almost no conversion had occurred, no further processing was undertaken. The asserted yield cannot be achieved with the described method. In particular, it must be pointed out that a major portion of the sulfuric acid is neutralized by N,N'-diphenyl-p-phenylenediamine (12 g correspond to 0.046 mol, meaning that only 0.019 mol of sulfuric acid is available as catalyst).

German patent application 199 20 796.8 filed May 6, 1999, is incorporated herein by reference.

What is claimed is:

1. A process for the synthesis of isobornyl (meth)acrylate comprising reacting camphene with (meth)acrylic acid in the presence of sulfuric acid and at least one polymerization inhibitor, wherein the sulfuric acid is aqueous sulfuric acid with an acid concentration in the range of 65 to 85 wt %.

2. A process according to claim 1, wherein the aqueous sulfuric acid has an acid concentration in the range of 70 to 80 wt %.

3. A process according to claim 1, wherein said inhibitor is a hydroquinone alkyl ether, a sterically hindered phenol and/or a sterically hindered piperidine N-oxyl derivative.

4. A process according to claim 1, wherein said inhibitor is a hydroquinone monomethyl ether, octadecyl-3-(3,5-di-tert-butyl-4-hydroxyphenyl)propionate or 4-hydroxy-2,2,6,6-tetramethylpiperidine N-oxyl, or a mixture of two or more of these compounds.

5. A process according to claim 1, wherein a chelating agent is present during reaction.

6. A process according to claim 5, wherein chelating agent is nitrilotriacetic acid, ethylenediaminetetraacetic acid, N-(2-hydroxyethyl)ethylenediaminetriacetic acid, 1,2-cyclohexylenedinitrilotetraacetic acid, diethylenetriaminepentaacetic acid, 3,6-dioxaoctamethylenedinitrilotetraacetic acid and/or an alkali metal salt of these acids.

7. A process according to claim 1, wherein the reaction takes place at a temperature in the range of 50 to 90° C.

8. A process according to claim 1, wherein after reaction the isobornyl (meth)acrylate is isolated by distillation in the presence of 2,6-di-tert-butyl-α-(dimethylamino)-p-cresol.

9. A process comprising distillating isobornyl (meth)acrylate from a mixture containing neutralized sulfuric acid, wherein distillation is performed in the presence of 2,6-di-tert-butyl-α-(dialkylamino)-p-cresol.

10. A process according to claim 9, characterized in that 2,6-di-tert-butyl-α-(dimethylamino)-p-cresol is the 2,6-di-tert-butyl-α-(dialkylamino)-p-cresol.

11. The process according to claim 1, wherein the esterification reaction medium contains from 100 to 500 ppm of hydroquinone monomethyl ether.

12. The process according to claim 1, wherein the esterification reaction medium contains octadecyl-3-(3,5-di-tert-butyl-4-hydroxyphenyl)propionate.

13. The process according to claim 1, wherein the esterification reaction medium contains 5 to 30 ppm of 4-hydroxy-2,2,6,6-tetramethylpiperidine N-oxyl.

* * * * *